(12) United States Patent
Hansmann et al.

(10) Patent No.: US 10,898,665 B2
(45) Date of Patent: Jan. 26, 2021

(54) SYSTEM FOR VENTILATING PATIENTS

(71) Applicant: Drägerwerk AG & Co. KGaA, Lübeck (DE)

(72) Inventors: Hans-Ullrich Hansmann, Barnitz (DE); Meinhard Braedel, Bargdeheide (DE); Karsten Hiltawsky, Stockelsdorf (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 289 days.

(21) Appl. No.: 15/814,812

(22) Filed: Nov. 16, 2017

(65) Prior Publication Data
US 2018/0133420 A1 May 17, 2018

(30) Foreign Application Priority Data

Nov. 17, 2016 (DE) .......................... 10 2016 013 740

(51) Int. Cl.
*A61M 16/00* (2006.01)
*A61M 16/12* (2006.01)
(Continued)

(52) U.S. Cl.
CPC .... *A61M 16/0066* (2013.01); *A61M 16/0063* (2014.02); *A61M 16/022* (2017.08);
(Continued)

(58) Field of Classification Search
CPC .......... A61M 16/0066; A61M 16/0816; A61M 16/022; A61M 16/201; A61M 16/1005;
(Continued)

(56) References Cited

U.S. PATENT DOCUMENTS 3,840,006 A * 10/1974 Buck ..................... A61M 16/00
128/204.21
2005/0244288 A1* 11/2005 O'Neill ............. A61M 16/0875
(Continued)

FOREIGN PATENT DOCUMENTS

DE 10 2012 024 672 A1 6/2014
JP 2000014784 A 1/2000
(Continued)

OTHER PUBLICATIONS

Goto, Taisuke, Notice of Reasons for Refusal: Japanese Patent Application No. 2017-220646, dated Dec. 25, 2019, Japan Patent Office.*
(Continued)

*Primary Examiner* — Samchuan C Yao
*Assistant Examiner* — Nathan M Le
(74) *Attorney, Agent, or Firm* — McGlew and Tuttle, P.C.

(57) ABSTRACT

A system (1) for ventilating patients includes a gas passage unit (2), which has a first inlet opening (6) with a fluid-communicating connection to a pressurized gas source (12, 13) and an outlet opening (9) connected to the first inlet opening (6) in a manner. A patient interface (3), for ventilation, includes an interface inlet opening (10). A gas line element (4) has a fluid-communicating connection to the outlet opening (9) and to the interface inlet opening (10). A controllable pressure change element (5) is provided between the first inlet opening (6) and the interface inlet opening (10). A second inlet opening (8) has a fluid-communicating connection to the gas line element (4). A control unit (7) controls the controllable pressure change element (5). A device or a system (1), which provides fully adequate ventilation with high performance with minimal expenditure for hardware, is provided.

19 Claims, 3 Drawing Sheets

(51) Int. Cl.
*A61M 16/10* (2006.01)
*A61M 16/20* (2006.01)
*A61M 16/08* (2006.01)

(52) U.S. Cl.
CPC .... *A61M 16/0816* (2013.01); *A61M 16/1005* (2014.02); *A61M 16/12* (2013.01); *A61M 16/201* (2014.02); *A61M 2016/003* (2013.01); *A61M 2016/0027* (2013.01); *A61M 2016/102* (2013.01); *A61M 2202/0208* (2013.01); *A61M 2205/0294* (2013.01)

(58) Field of Classification Search
CPC .... A61M 2202/0208; A61M 2016/102; A61M 2016/003; A61M 2016/0027; A61M 2205/0294; A61M 16/0063; A61M 16/12; A61M 16/0057; A61M 16/006; A61M 16/20; A61M 16/202; A61M 16/203; A61M 16/204; A61M 16/205
See application file for complete search history.

(56) References Cited

U.S. PATENT DOCUMENTS

| | | | | |
|---|---|---|---|---|
| 2009/0312661 | A1* | 12/2009 | Kullik | A61B 5/0876 600/538 |
| 2014/0261422 | A1* | 9/2014 | Lang | A61M 16/0051 |
| 2014/0305436 | A1* | 10/2014 | Nitta | F04B 19/006 128/204.25 |
| 2015/0040904 | A1* | 2/2015 | Nitta | A61M 16/203 128/204.23 |
| 2015/0059749 | A1* | 3/2015 | Nitta | A61M 16/0012 128/204.18 |
| 2015/0101610 | A1* | 4/2015 | Nitta | A61M 16/205 128/204.25 |
| 2015/0267695 | A1* | 9/2015 | Marsh | F16K 1/18 128/205.24 |
| 2015/0328417 | A1* | 11/2015 | Loser | A61M 16/024 |
| 2015/0335851 | A1* | 11/2015 | Cullen | A61M 16/0057 128/204.25 |
| 2016/0015918 | A1* | 1/2016 | Kuriger | A61M 16/0069 128/204.23 |
| 2016/0061742 | A1* | 3/2016 | Rostalski | G01N 21/272 436/171 |
| 2016/0220780 | A1* | 8/2016 | Nitta | A61M 16/204 |
| 2016/0287824 | A1* | 10/2016 | Chang | A61M 16/1005 |
| 2016/0310769 | A1* | 10/2016 | Tang | A62B 9/003 |
| 2017/0113014 | A1* | 4/2017 | Nitta | A61M 16/06 |
| 2017/0259019 | A1* | 9/2017 | Cariola | A61M 16/021 128/204.21 |
| 2018/0093063 | A1* | 4/2018 | Rajan | A61M 16/0816 |
| 2018/0177961 | A1* | 6/2018 | Kagan | A61M 16/024 |

FOREIGN PATENT DOCUMENTS

| | | |
|---|---|---|
| JP | 2004-298554 A | 10/2004 |
| JP | 2007-296359 A | 11/2007 |
| JP | 2013-512716 A | 4/2013 |
| JP | 2014-180304 A | 9/2014 |

OTHER PUBLICATIONS

Garimella, Raghu, et. al., Piezo-Gen—An Approach to Generate Electricity from Vibrations, 2015, Procedia Earth and Planetary Science 11 (2015) 445-456.*
Resonance, Aug. 23, 1996, Institute for Telecommunication Sciences, webpage, https://www.its.bldrdoc.gov/fs-1037/dir-031/_4576.htm.*

* cited by examiner

SYSTEM FOR VENTILATING PATIENTS

CROSS REFERENCE TO RELATED APPLICATIONS

This application claims the benefit of priority under 35 U.S.C. § 119 of German Application 10 2016 013 740.1, filed Nov. 17, 2016, the entire contents of which are incorporated herein by reference.

FIELD OF THE INVENTION

The present invention pertains to a system for ventilating patients, which has a patient interface unit for ventilation with an interface inlet opening, a gas line element, which is connected to the interface inlet opening in a fluid-communicating manner, and a control unit.

BACKGROUND OF THE INVENTION

The ventilation of patients is carried out in hospitals with stationary and mobile devices (ventilators also known as respirators). Depending on how well a patient can or cannot breathe on their own, a stationary device or a mobile device is used. Stationary devices are used for patients who are no longer able to breathe spontaneously or are able to do so with great difficulties only. Mobile devices are used for patients who only require a slight support for breathing. Further, mobile ventilators are used to wean patients who were hitherto ventilated stationarily from the ventilators.

Stationary ventilators comprise gas mixers, a pressure/volume control, safety devices, energy supply devices, a global control, monitoring devices and operating devices. They are complex and heavy and are not suitable for being carried along by the patients. The ventilation is carried out here via disposable tubes with diameters of about 18 mm and masks. Expiration valves, which were brought into contact with exhaled air possibly contaminated by microorganisms are either processed or configured as disposable articles. In case of high performance, these devices are large and expensive.

Furthermore, CPAP (continuous positive airway pressure) devices are known, which provide a continuous pressure. In addition, high-flow systems are known, which comprise blenders/gas mixers, humidifiers and a cannula. These two device classes are used for patients who can breathe on their own and need only a very slight ventilation support. The drawback of these device classes is that they do not permit assisted support and mandatory ventilation modes.

SUMMARY OF THE INVENTION

An object of the present invention is therefore to provide a device and a system that provide fully adequate ventilation with high performance, while the expenditure for hardware shall be minimal.

Provisions are made according to the present invention for a system for ventilating patients, which comprises a gas passage unit, which has a first inlet opening for connecting a pressurized gas source and an outlet opening connected to the first inlet opening in a fluid-communicating manner; a patient interface unit for ventilation, which comprises an interface inlet opening; a gas line element, which connects the outlet opening to the interface inlet opening in a fluid-communicating manner; a first controllable pressure change element between the first inlet opening and the interface inlet opening; a second inlet opening, which is connected to the gas line element in a fluid-communicating manner; and a control unit for controlling the controllable pressure change element.

A pressure difference can be established between the gas passage unit and the patient interface unit by means of the controllable pressure change element between the gas passage unit, which has the first inlet opening, and the patient interface unit, which has the interface inlet opening. A high pressure can be applied in this manner at the gas passage unit, and a low pressure is applied at the patient interface unit. For example, an oxygen gas cylinder or a pressurized oxygen supply unit may now be connected to the first inlet opening. Such a high pressure will now prevail at the gas passage unit that is at first unsuitable for inhalation by a patient. This high pressure is reduced on the side of the patient interface unit by means of the controllable pressure change element to the extent that a patient, who is breathing through the patient interface unit, can be comfortably ventilated. Pressure fluctuations on the side of the gas passage unit are compensated by means of the controllable pressure change element, so that a physiologically useful pressure will always prevail at the patient interface unit. Any desired pressure source can thus be used to ventilate a patient due to the use of the pressure change element between the gas passage unit and the patient interface unit. It is thus possible to use, for example, wall-mounted supply units, which provide pressurized oxygen, to ventilate the patient. An assisted or mandatory ventilation may consequently take place. Even patients who require a great support during breathing can be reliably ventilated with high performance by means of the present invention.

Further, the present invention makes it possible to ventilate patients with high performance under mobile conditions, because only the compressed air cylinder needs to be moved along with the patient bed if a compressed air cylinder is used. Contrary to the state of the art, it is now no longer necessary to move the entire, heavy ventilator, which also requires a continuous power supply. Unlike in the case in which CPAP devices or high-flow devices are used, even patients who require intensive support during ventilation or even have to have mandatory ventilation are now mobile.

The expenditure for hardware can thus be kept at a minimum by means of the present invention with a high, fully adequate ventilation performance. Conventional gas sources can thus be used independently from ventilators. The performance is just as in the case of conventional ventilators, but the system according to the present invention is smaller, has a lower weight and can be operated in a more favorable and simpler manner.

The pressure change element is advantageously a precision control valve. A pressure between the gas passage unit and the patient interface unit drops at the precision control valve. If there is no flow of gas, the pressure drop does not develop at the precision control valve, so that a high pressure builds up at the line to the mask, i.e., between the precision control valve and the first inlet opening. As soon as gas can again flow in the direction of the mask, the high pressure will be reduced rapidly. Risk to the patient can thus be ruled out in case of a simple error. As an alternative, the controllable pressure change element may be configured as a quick-acting pressure reducer.

The patient interface unit advantageously comprises a controllable gas outlet valve and which is connected to the interface inlet opening in a fluid-communicating manner.

The second inlet opening is advantageously arranged at the gas line element. In this case, the second inlet opening may be configured as a Venturi nozzle.

The second inlet opening may advantageously be arranged, as an alternative, at the gas passage unit. A second high-pressure source can thus be connected to the gas passage unit. When different gases or gas mixtures are introduced at the first and second inlet openings, the two gases or gas mixtures can be mixed with one another in the gas passage unit on their way to the outlet opening. Physiologically useful gas mixtures can thus be provided for the patient.

A second controllable pressure change element is advantageously provided between the second inlet opening and the interface inlet opening and connected in a fluid-communicating manner.

It may further be advantageous to arrange a humidifying device between the outlet opening and the interface inlet opening. By arranging the humidifying device in the gas path between the outlet opening and the interface inlet opening, dry air from gas cylinders or from wall-mounted supply units can be humidified. Furthermore, breathing air processed in a physiologically useful manner can be fed to the patient. The humidifying device is preferably connected to the gas line element.

A gas concentration sensor, preferably for oxygen, may advantageously be arranged between the outlet opening and the interface inlet opening. A concentration of certain gases, for example, oxygen, can be measured with the gas concentration sensor, and this concentration can then be set by means of the control unit and the controllable pressure change element to a concentration that shall be fed to the patient.

It may further be advantageous to arrange a flow sensor between the outlet opening and the interface inlet opening. The gas flow between the outlet opening and the interface inlet opening can be measured with the flow sensor.

The first inlet opening is advantageously connected to a pressurized oxygen source. Furthermore, the second inlet opening may advantageously be connected to a pressurized room air source or a room air source. Room air under pressure can be enriched in this manner with oxygen and fed to the patient.

It is advantageous to configure the patient interface unit as a mask, preferably as a nasal mask. A patient can be comfortably ventilated in this manner.

Furthermore, a user interface, which may be connected to the control unit via a signal connection, is advantageously provided for operating the control unit. The signal connection may be a wired or wireless connection.

The user interface is advantageously configured as a smartphone, on which a control program (app/application) provides an input mask for the values of the system, which are to be set. An input mask, which can be operated by the staff or even by the patient himself or herself based on instructions, can be provided in this way in a simple manner. Instead of a smartphone, a tablet or another portable computer may be used as a user interface. A simple touchscreen may likewise be used as a user interface.

A pressure sensor is advantageously arranged at the patient interface component. The controllable pressure change elements may be controlled in this case by the control unit on the basis of the signals of the pressure sensor. The ventilation system may be used independently from the input pressure at the inlet openings in this manner.

The gas line element may, furthermore, advantageously have a free diameter between 5 mm and 15 mm, preferably 10 mm. Due to the control of the pressure by means of the pressure change element, a pressure drop, which is brought about by the diameter of the gas line element between the outlet opening and the interface inlet opening, can be compensated by a correspondingly higher pressure at the outlet opening. The diameter of the gas line element may therefore be selected in a flexible manner, especially as a diameter that is smaller than in the state of the art. As a result, thinner gas line elements, which are flexible and lightweight, can be used compared to the state of the art. Mobility is facilitated for the patient by the more flexible, thinner and hence more lightweight gas lines.

The present invention will be explained in more detail below on the basis of the attached drawings by means of an advantageous exemplary embodiment.

The present invention will be described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
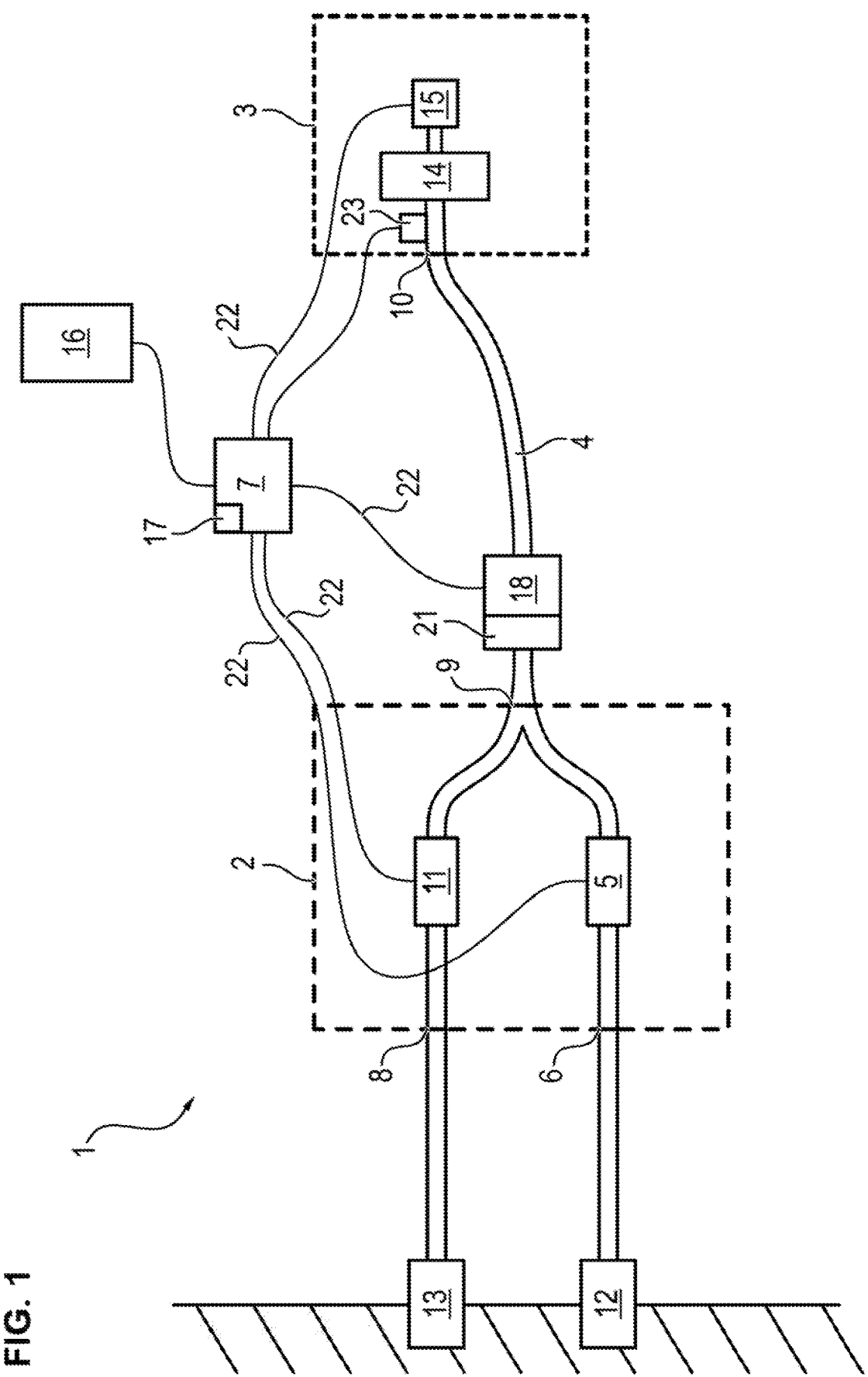
FIG. 1 is a schematic view of a ventilation system, which is connected to two wall-mounted gas supply lines.

Referring to the drawings, the ventilation system is designated below in its entirety by the reference number 1.

The system 1 comprises a gas passage unit 2, a patient interface unit 3 as well as a gas line element 4. The gas line element 4 connects an outlet opening 9 of the gas passage unit 2 to an interface inlet opening 10 of the patient interface unit 3 in a fluid-communicating manner.

The gas passage unit 2 further comprises a first inlet opening 6 as well as a second inlet opening 8. The first and second inlet openings 6, 8 are connected to the outlet opening 9 in a fluid-communicating manner. A first controllable pressure change element 5 is arranged between the first inlet opening 6 and the outlet opening 9. The controllable pressure change element 5 may be configured as a quick-acting pressure reducer or as a quick-acting precision control valve. The first controllable pressure change element 5 changes a high pressure at the first inlet opening 6 into a pressure at the outlet opening 9, which is lower than at the first inlet opening 6.

Further, a second controllable pressure change element 11 is arranged between the second inlet opening 8 and the outlet opening 9. The second controllable pressure change element 11 changes a high pressure at the second inlet opening 8 into a pressure at the outlet opening 9, which is lower than at the second inlet opening 8.

A high-pressure gas source 12, 13 each can therefore be connected to the first and second inlet openings 6, 8. This high-pressure gas source is connected in FIG. 1 as a pressurized oxygen source 12 at the first inlet opening 6 and is connected as a pressurized air source 13 to the second inlet opening 8.

The high pressures at the first and second inlet openings 6, 8 are converted by the controllable pressure change elements 5, 11 into a physiologically useful pressure. This physiologically useful pressure is then applied to the patient interface unit 3 via the outlet opening 9 and the gas line element 4. Pressure fluctuations or pressure drops are compensated by the controllable pressure change elements 5, 11, so that the same pressure or a physiologically useful pressure is always applied at the outlet opening 9, and this pressure is then passed on to the patient interface unit 3. Fully adequate ventilation can be guaranteed in this manner with simple means.

Furthermore, the pressure at the outlet opening 9, i.e., at the patient interface unit 3, can be changed by means of the controllable pressure change elements 5, 11. High pressures can be used at the patient in this manner for a phase of inhalation and lower pressures for a phase of exhalation. As long as a minimum pressure is present at the inlet openings 6, 8, ventilation of a patient can take place by means of the controllable pressure change elements 5, 11.

The interface to the patient is established via the patient interface unit 3. The patient interface unit 3 comprises a mask 14, which is placed on the patient's face and encloses at least the patient's nose. As an alternative, the mask 14 may enclose at least the patient's mouth.

The patient interface unit 3 further comprises a controllable (expiration (exhalation) valve 15. The expiration valve 15 is arranged at the mask 14.

Figure 3:
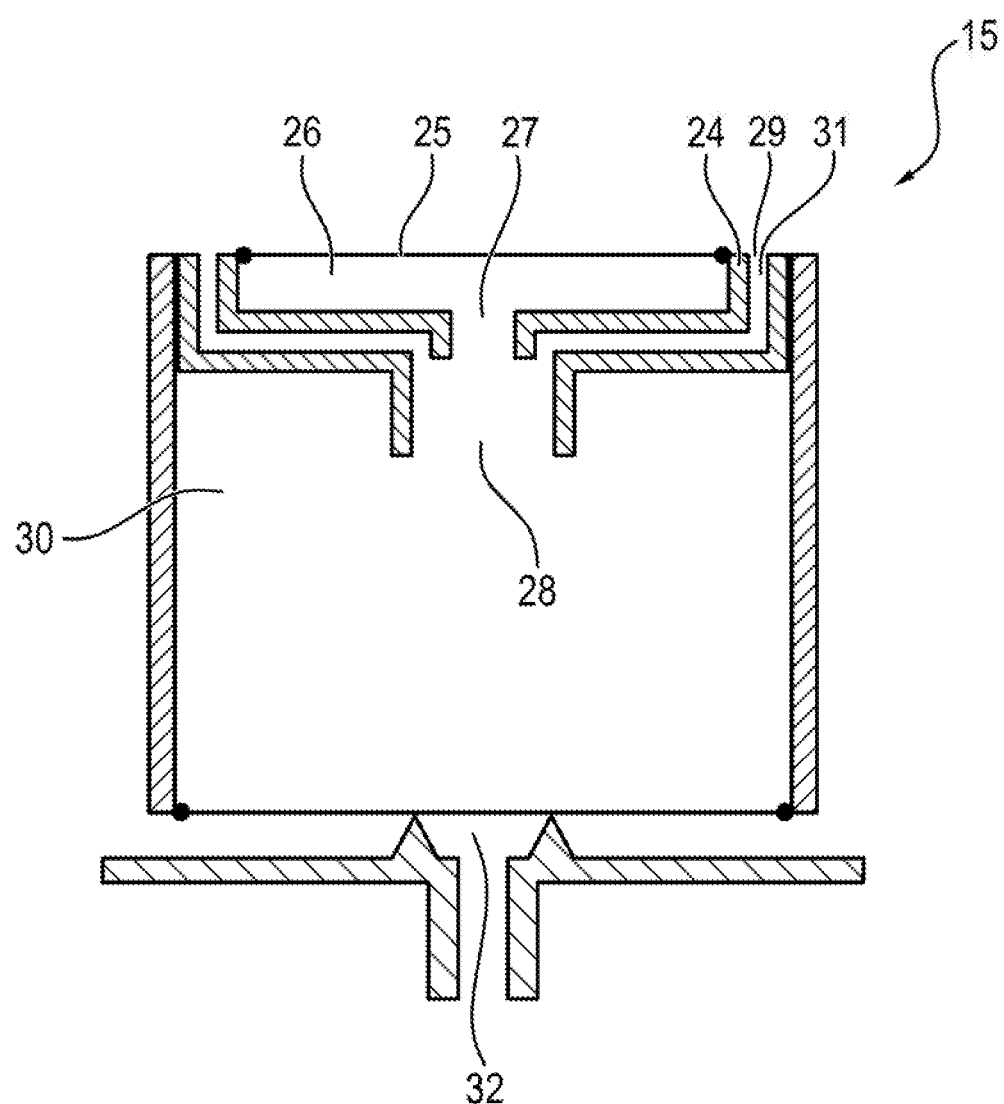
FIG. 3 is a schematic view of a controllable exhalation (expiration) valve.

It (expiration) valve 15 has a drive 24 according to FIG. 3, which acts on a control pressure chamber 30, wherein a wall of the control pressure chamber 30 acts on a valve opening of the expiration valve 15.

The drive 24 of the expiration valve 15 is a piezo pump, through which flow is possible in two directions. The piezo pump has a pump chamber 26 with a pump opening 27. A wall of the pump chamber 26 is configured as a diaphragm 25, on which an oscillating piezo element acts. The oscillation may be brought about by means of a controllable alternating current. The alternating current has a frequency of about 25 kHz in this embodiment.

The pump opening 27 is arranged at a pump line 31 with two end openings 28, 29. A first end opening 28 is arranged at the control pressure chamber 30. A second end opening 29 is connected to the surrounding area in a fluid-communicating manner (with a fluid communicating connection). When the drive 24 is switched on, the oscillation of the Piezo element brings about an oscillation of the diaphragm 25. As a result, the volume of the pump chamber 26 is increased or reduced in an oscillating manner. Fluid is ejected with a linear flow from the pump opening 27 during the reduction of the volume of the pump chamber 26. The fluid flowing out of the pump opening 27 in this case produces a directed flow in the pump line 31, which is directed into the control chamber 30. When the drive 24 is switched off, there is no directed flow in the pump line 31, so that the control pressure chamber 30 is connected to the surrounding area via the pump line 31 such that a pressure equalization can take place between the control pressure chamber 30 and the surrounding area.

The system 1 further has a control unit 7, which is connected to the controllable pressure change elements 5, 11 and the exhalation valve 15 via signal connections 22. The control unit 7 can control the controllable pressure change elements 5, 11 as well as the expiration valve 15 via the signal lines 22.

The control unit 7 can be operated by means of a user interface 16. User parameters can be transmitted to the control unit 7 via the user interface 16. These parameters may be, for example, set points or limit values for ventilation-relevant variables. The user interface 16 may be configured as a smartphone or as a tablet. The user interface 16 may be configured in other alternatives as a touchscreen or another suitable device.

A user interface 16 configured as a smartphone or tablet may be carried along by the health care staff. A computer program on the smartphone or the tablet now performs the communication with the control unit 7. The health care staff can thus also actuate a plurality of ventilation systems 1 with one user interface 16 by the computer program exchanging communication signals assigned unambiguously to a defined system 1 with each system 1. Furthermore, the systems 1 may be controlled remotely with the user interface 16 configured as a smartphone or tablet.

Furthermore, a patient is enabled to make fine adjustments by means of the user interface 16 when he or she needs more or less support while breathing through the system 1.

The gas line element 4 may further have a humidifying module 21, which humidifies the breathing air sent to the patient interface unit 3. The reason for this is that the air taken from the wall-mounted supply devices or gas cylinders is usually very dry and therefore unsuitable for patients. Humidification is therefore necessary in order to establish a physiologically useful humidity in the breathing air, which is sent to the patient.

The gas line element 4 further comprises a gas concentration sensor 18. The gas concentration sensor 18 is configured in this embodiment to determine oxygen. The oxygen concentration in the air fed to the patient interface unit 3 can thus be measured. The gas sensor 18 transmits the measured data to the control unit 7, which checks them to determine whether the measured oxygen concentration corresponds to the desired oxygen concentration. In case of deviations, the control unit 7 determines how the controllable pressure change elements 5, 11 must be set to obtain a desired gas concentration. This can happen, as an alternative, via a control circuit. The controllable pressure change elements 5, 11 are then actuated via the signal connections 22 by the control unit 7 in a suitable manner.

The gas line element 4 is configured as a tube with a diameter of 10 mm. A tube with this diameter is lighter and more flexible than the conventional tubes with a diameter of 18 mm. The smaller diameter is made possible by the controllable pressure change elements 5, 11, which take the pressure drop caused by the tube diameter into consideration by a correspondingly higher pressure at the outlet opening 9 of the gas passage unit 2.

Furthermore, a pressure sensor 23, which measures the pressure at the interface inlet opening 10, is arranged at the patient interface unit 3. The pressure sensor 23 is connected to the control unit 7 via a signal connection 22 and transmits the determined pressure signals to the control unit 7. The control unit 7 can compensate the pressure drop in the gas line element 4 by means of the pressure signals by corresponding actuation of the controllable pressure change elements 5, 11.

The control unit 7 further comprises an energy source element 17, which may be configured as a battery. The control unit can thus be operated independently from the power grid. The control unit 7 can be set by a user to certain parameters via a user interface 16.

Figure 2:
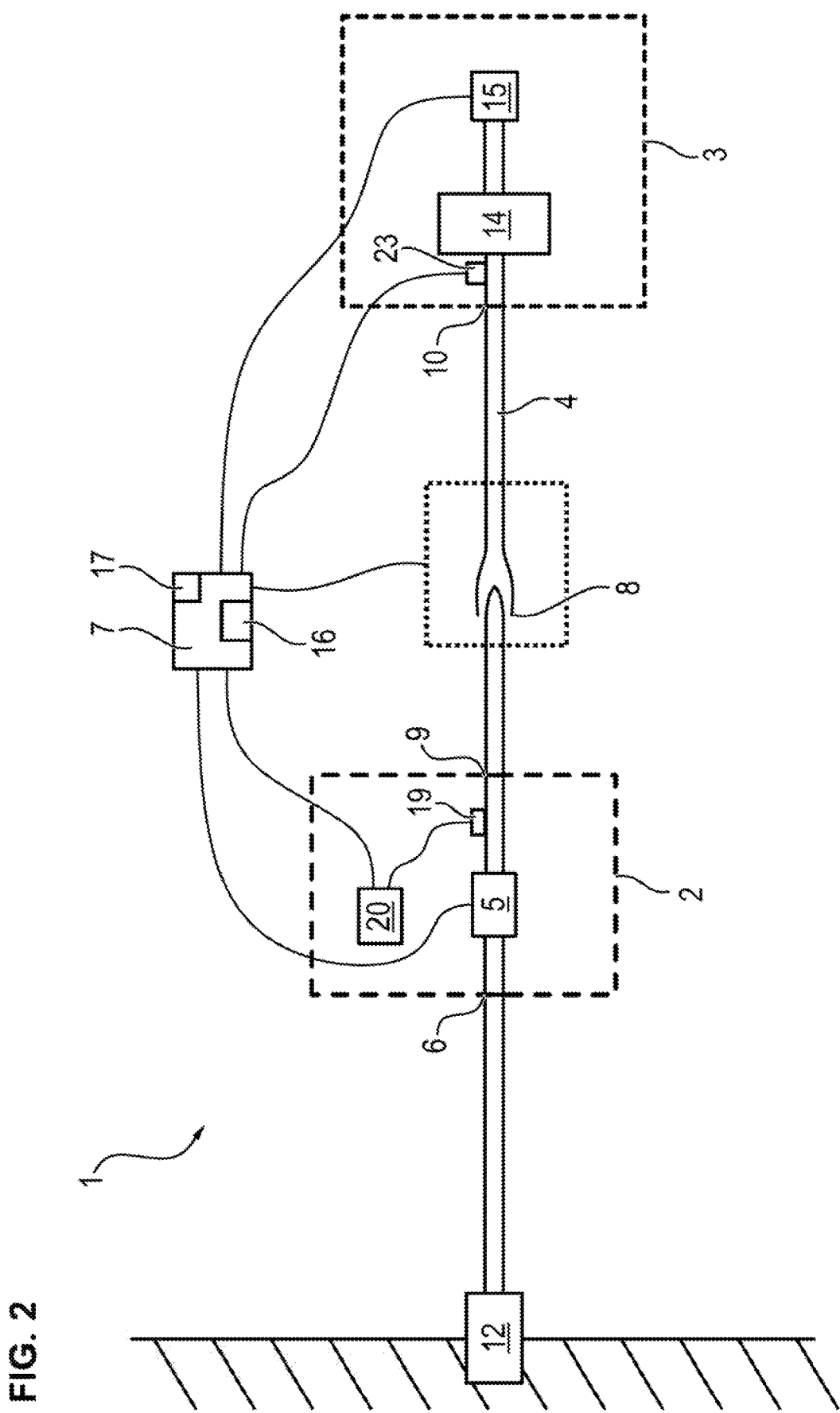
FIG. 2 is a schematic view of a ventilation system with a wall-mounted connection and a Venturi nozzle.

FIG. 2 shows an alternative embodiment of the system 1. According to FIG. 2, the ventilation system 1 comprises a gas passage unit 2 with a first inlet opening 6, which is connected to a pressurized oxygen source 12 in a fluid-communicating manner. The gas passage unit 2 further comprises an outlet opening 9, which is connected to the first inlet opening 6 in a fluid-communicating manner. The first controllable pressure change element 5 is arranged between the first inlet opening 6 and the outlet opening 9.

A gas line element 4, which connects the gas passage unit 2 to the patient interface unit 3 in a fluid-communicating manner, is connected to the outlet opening 9. The gas line element 4 is connected at the patient interface unit 3 to an interface inlet opening 10 in a fluid-communicating manner.

The gas line element 4 further comprises a second inlet opening 8 in the form of a Venturi nozzle. Room air is drawn through the second inlet opening 8 into the gas line element 4 by the gas stream, which flows through the second inlet opening 8. A mixture of oxygen and room air is formed as a result.

The patient interface unit 3 shown in FIG. 2 has a configuration corresponding to the patient interface unit 3 shown in FIG. 1.

The gas passage unit 2 further comprises a flow sensor 19, which detects the gas flow between the first controllable pressure change element 5 and the outlet opening 9. The value of the gas flow is transmitted to a display element 20, which displays the gas flow.

The signal of the flow sensor 19 is further transmitted to a control unit 7. The control unit 7 controls the first controllable pressure change element 5 by means of the signal. The control unit 7 may furthermore monitor the Venturi nozzle and the second inlet opening 8 and optionally control the size of the second inlet opening 8. The expiration valve 15 may also be controlled by the control unit 7.

Fully adequate ventilation with high performance can be carried out in this manner by means of a cost-effective high-pressure source for a patient to be ventilated.

While specific embodiments of the invention have been shown and described in detail to illustrate the application of the principles of the invention, it will be understood that the invention may be embodied otherwise without departing from such principles.

APPENDIX

List of reference numbers

| | |
|---|---|
| 1 | System |
| 2 | Gas passage unit |
| 3 | Patient interface unit |
| 4 | Gas line element |
| 5 | First controllable pressure change element |
| 6 | First inlet opening |
| 7 | Control unit |
| 8 | Second inlet opening |
| 9 | Outlet opening |
| 10 | Interface inlet opening |
| 11 | Second controllable pressure change element |
| 12 | Pressurized oxygen source |
| 13 | Air pressure source |
| 14 | Mask |
| 15 | Exhalation valve |
| 16 | User interface |
| 17 | Energy source element |
| 18 | Gas concentration sensor |
| 19 | Flow sensor |
| 20 | Display element |
| 21 | Humidifying module |
| 22 | Signal connection |
| 23 | Pressure sensor |

APPENDIX-continued

List of reference numbers

| | |
|---|---|
| 24 | Drive |
| 25 | Diaphragm |
| 26 | Pump chamber |
| 27 | Pump opening |
| 28 | First end opening |
| 29 | Second end opening |
| 30 | Control pressure chamber |
| 31 | Pump line |
| 32 | Valve opening |

What is claimed is:

1. A system for ventilating patients, the system comprising:
a gas passage unit comprising a first inlet opening for connecting a pressurized gas source and an outlet opening with a fluid-communicating connection to the first inlet opening;
a patient interface unit for supplying breathing gas to a patient and removing breathing gas from the patient interface unit of a patient breathing, through the patient interface unit for ventilation of the patient,
wherein the patient interface unit comprises:
an interface inlet opening; and
a controllable expiration valve comprises:
an expiration valve opening for the breathing gas to be removed from the patient interface unit to outside of the patient interface unit; and
an expiration valve drive comprising a piezo pump controlled by an alternating current, the piezo pump being controlled to pump gas to a pressure chamber to control a gas pressure in the pressure chamber, which the gas pressure in the pressure chamber affects an action of a pressure chamber membrane wall on the expiration valve opening, to control the pressure chamber membrane wall acting on the expiration valve opening of the expiration valve to control a patient interface unit expiration pressure at the expiration valve opening;
a gas line element providing a fluid-communicating connection of the outlet opening to the interface inlet opening;
a controllable pressure change element between the first inlet opening and the interface inlet opening, the controllable pressure change element being configured to convert a high pressure at the first inlet opening into a physiologically useful breathing gas pressure at the interface inlet opening, which the physiologically useful breathing gas pressure is lower than the high pressure at the first inlet opening;
a second inlet opening with a fluid-communicating connection to the gas line element; and
a control unit configured to control the controllable pressure change element and to control the expiration valve drive.

2. The system for ventilating patients in accordance with claim 1, wherein the controllable pressure change element is a precision control valve.

3. The system for ventilating patients in accordance with claim 1, wherein the second inlet opening is arranged at the gas line element, wherein the second inlet opening is configured as a Venturi nozzle.

4. The system for ventilating patients in accordance with claim 1, wherein the second inlet opening is arranged at the gas passage unit.

5. The system for ventilating patients in accordance with claim 4, further comprising a second controllable pressure change element with a fluid-communicating connection between the second inlet opening and the interface inlet opening, the second controllable pressure change element being connected with a fluid-communicating connection.

6. The system for ventilating patients in accordance with claim 1, further comprising a humidifying device arranged between the outlet opening and the interface inlet opening.

7. The system for ventilating patients in accordance with claim 1, further comprising a gas concentration sensor for sensing oxygen concentration arranged between the outlet opening and the interface inlet opening.

8. The system for ventilating patients in accordance with claim 1, further comprising a flow sensor arranged between the first inlet opening and the interface inlet opening.

9. The system for ventilating patients in accordance with claim 1, wherein the first inlet opening is connected to a pressurized oxygen source and the second inlet opening is connected to a pressurized room air source or to a room air source.

10. The system for ventilating patients in accordance with claim 1, wherein the patient interface unit is configured as a mask.

11. The system for ventilating patients in accordance with claim 10, wherein the patient interface unit is configured as a nasal mask.

12. The system for ventilating patients in accordance with claim 1, further comprising a user interface for operating the control unit, the user interface being connected to the control unit via a signal connection.

13. The system for ventilating patients in accordance with claim 12, wherein the user interface is configured as a smartphone, tablet or portable computer, on which a control program provides controlling of user parameters for ventilation-relevant variables of the system, which are to be set.

14. The system for ventilating patients in accordance with claim 1, wherein a pressure sensor is arranged at the patient interface unit.

15. The system for ventilating patients in accordance with claim 1, wherein the gas line element has a diameter between 5 mm and 15 mm.

16. A system for ventilating patients, the system comprising:
a gas passage unit comprising a first inlet opening for connecting a pressurized gas source and an outlet opening with a fluid-communicating connection to the first inlet opening;
a patient interface unit for supplying breathing gas to a patient and removing breathing gas from the patient interface unit of a patient breathing through the patient interface unit for ventilation of the patient,
wherein the patient interface unit comprises:
an interface inlet opening; and
a controllable expiration valve, the controllable expiration valve comprising:
an expiration valve opening for passage of gas from the patient interface unit to outside of the patient interface unit to remove the breathing gas from the patient interface unit;
a pressure chamber with a pressure chamber membrane wall acting on the expiration valve opening and configured to act on the expiration valve opening based on a gas pressure within the pressure chamber, wherein the gas pressure within the pressure chamber affects an a movement action of the pressure chamber membrane wall relative to the expiration valve opening; and
an expiration valve drive comprising a piezo pump controlled by an alternating current, the piezo pump being controlled to pump gas to the pressure chamber to affect the gas pressure within the pressure chamber that acts on the pressure chamber membrane wall to control a patient interface unit expiration pressure at the expiration valve opening based on the gas pressure within the pressure chamber;
a gas line element providing a fluid-communicating connection of the outlet opening to the interface inlet opening;
a controllable pressure change element between the first inlet opening and the interface inlet opening, the controllable pressure change element being configured to convert a high pressure at the first inlet opening into a physiologically useful breathing gas pressure at the interface inlet opening, which the physiologically useful breathing gas pressure is lower than the high pressure at the first inlet opening;
a second inlet opening with a fluid-communicating connection to the gas line element; and
a control unit configured to control the controllable pressure change element and to control the expiration valve drive.

17. The system for ventilating patients in accordance with claim 16, wherein the controllable pressure change element is a precision control valve.

18. The system for ventilating patients in accordance with claim 16, wherein the second inlet opening is arranged at the gas line element, wherein the second inlet opening is configured as a Venturi nozzle.

19. The system for ventilating patients in accordance with claim 16, wherein the second inlet opening is arranged at the gas passage unit and further comprising a second controllable pressure change element with a fluid-communicating connection between the second inlet opening and the interface inlet opening, the second controllable pressure change element being connected with a fluid-communicating connection.

* * * * *